United States Patent [19]

Nevel

[11] Patent Number: 4,531,400
[45] Date of Patent: Jul. 30, 1985

[54] METHOD AND APPARATUS FOR ICE IMPACT TESTING

[75] Inventor: Donald E. Nevel, Carrollton, Tex.

[73] Assignee: Mobil Oil Corporation, New York, N.Y.

[21] Appl. No.: 538,303

[22] Filed: Oct. 3, 1983

[51] Int. Cl.³ .......................... G01N 3/30; G01N 3/48
[52] U.S. Cl. ............................................ 73/12; 73/82
[58] Field of Search .................. 73/12, 82, 78, 79, 81, 73/83, 84, 85, 87, 170 A, 432 Z, 432 SD, 856; 374/46

[56] References Cited

U.S. PATENT DOCUMENTS

| | | | |
|---|---|---|---|
| 2,986,922 | 6/1961 | Garofalo et al. | 374/46 |
| 3,583,215 | 6/1971 | Franz | 73/12 X |
| 3,618,369 | 11/1971 | Hamilton et al. | 73/81 |
| 3,998,090 | 12/1976 | Wislocki | 73/12 |
| 4,313,337 | 2/1982 | Myint | 73/12 |

FOREIGN PATENT DOCUMENTS 1104953  3/1968  United Kingdom ................... 73/12

Primary Examiner—Charles A. Ruehl
Attorney, Agent, or Firm—A. J. McKillop; Michael G. Gilman; Frank J. Kowalski

[57] ABSTRACT

A method and apparatus for impact testing ice in a laboratory environment simulates in-situ conditions wherein an ice sample is confined triaxially and maintained at a controlled temperature to approximate a semi infinite mass. An impact device impinges on the ice sample so confined.

9 Claims, 2 Drawing Figures

METHOD AND APPARATUS FOR ICE IMPACT TESTING

BACKGROUND OF THE INVENTION

The present invention relates to testing for various properties of ice samples and more particularly to testing for impact properties of a large ice mass such as an iceberg.

Offshore environments are becoming increasingly important as a food source and as an energy source. For example, as land based hydrocarbon fuel sources are exhausted, reliance on offshore sources for hydrocarbon fuel is enhanced. Design criteria for offshore facilities, such as an oil production or drilling platform include wave height, wind velocity etc. However, particularly in the north Atlantic, structural designs must include provision for impact by a solid mass such as an iceberg.

Many methods of testing ice have been developed under a variety of conditions. These types of tests may be performed in the field as well as in a laboratory cold room where the temperature may be controlled.

The types of impact tests that have previously been performed are those associated with crack propagation such as the Charpy impact test, penetration of a rigid indentor into or through the ice, a weight impacting a uniaxial specimen, or a rigid sphere dropped on a flat ice surface. Of these kinds of tests, the sphere dropped on a flat ice surface best represents the ice failure mechanism which will occur when an iceberg collides with an offshore structure. That is a blunt rigid body impacting a rather blunt large ice mass in which the ice becomes crushed at the area of contact and gets squeezed out between the two bodies.

Up until now this kind of testing has been done by transporting a large impact device to the location where ice is to be tested. Normally, these methods and apparatus are only suitable for impact testing a stable, immovable ice mass such as a frozen surface of a lake, river or other large body of water. Whenever the ice mass to be tested is unstable or movable, such as ice floating in water, impact testing is not meaningful.

In order for impact testing to be meaningful for offshore structures, either the ice or the impact device must be firmly positioned. A small ice mass floating in water is not satisfactorily positioned to absorb the force of an impact device. As a result, the ice mass will deflect away from the force imposed by the impact device and give little or no indication of the impact.

An iceberg, such as that found in the north Atlantic, may range up to one hundred million tons. Due to the temperature difference between ambient air and water, the portion of the iceberg above the surface of water will melt at a different rate from that below the surface. As such, the center of gravity of the iceberg will constantly shift causing the iceberg to roll in the water.

SUMMARY OF THE INVENTION

The present invention provides a method and apparatus for impact testing of ice samples under laboratory conditions which simulate actual environment. An ice sample is precut into a short disc like cylinder and placed in a close fitting annular frame. The frame is backed on one side by a flat sheet of like material, both frame and backing sheet having a high tensile strength, density, and low ductility. The frame and backing are placed on a solid structure fixed to the earth's surface. An impact device is brought in contact with the ice sample, which together with the frame, has triaxial stability.

DESCRIPTION OF THE PREFERRED EMBODIMENT

Figure 1:
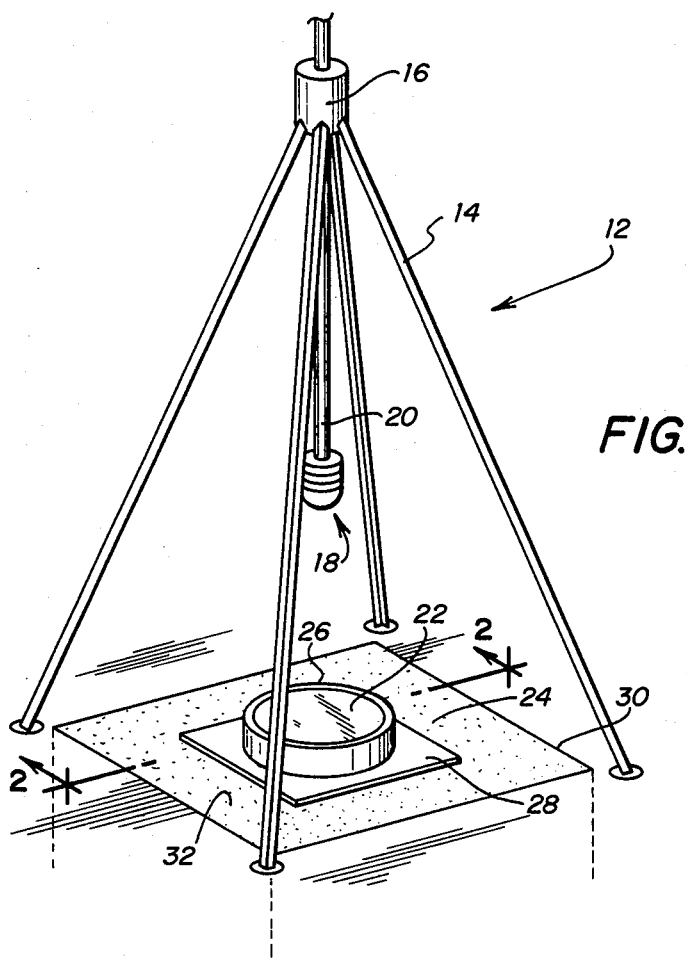
FIG. 1 is a perspective view of an ice impact testing system.

The present invention provides a method and apparatus for obtaining meaningful impact data from ice sample testing in a laboratory environment. Referring to FIG. 1, ice sample testing system 12 is illustrated as having structure 14 with guide cylinder 16 releasably holding impact device 18 mounted at the end of shaft 20. Positioned within structure 14 and below impact device 18 is ice sample 22 frozen within frame 24. Frame 24 consists of an annular shaped ring 26 and backing plate 28. Backing plate 28 is fixed within pit 30 which is filled with support material 32.

Ring 26 and backing plate 28 are preferably aluminum or steel, however, any suitable material for providing triaxial support for ice sample 22. In the preferred embodiment, the thickness of ring 26 may be calculated according to formula as listed in Appendix A.

Figure 2:
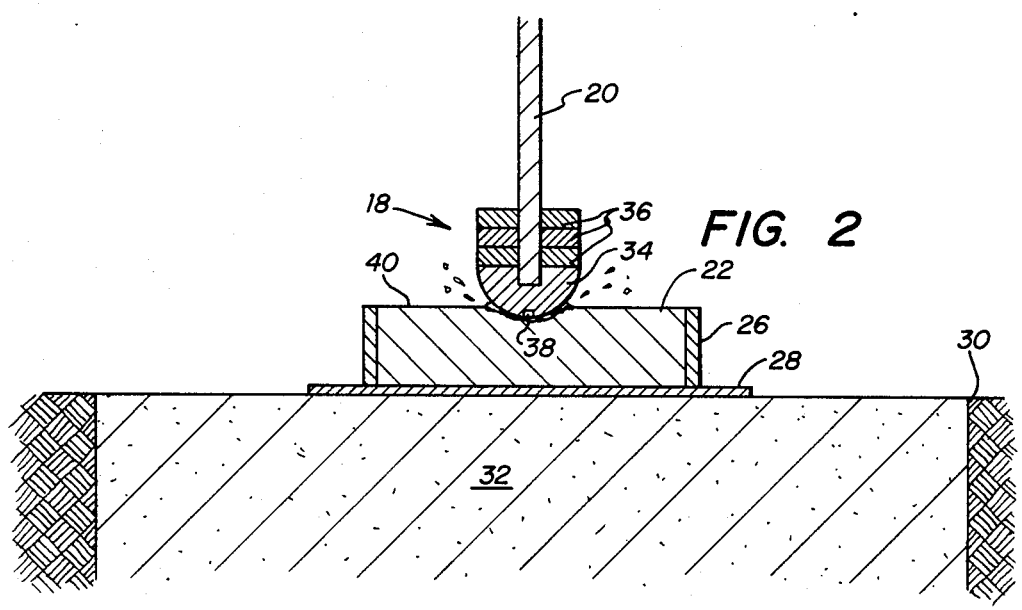
FIG. 2 is a side sectional view of the base of FIG. 1.

Referring now to FIG. 2, impact device 18 is illustrated as comprising spherically shaped head 34 and a plurality of weights 36. Ring 26 is illustrated as being fixed to backing plate 28. Preferably, ring 26 is welded to the base of 28 to provide a confining structure for ice sample 22. Ice sample 22 may be cut in a disc shape and inserted into frame 24. Any space existing between ice sample 22 and frame 24 is preferably filled with a fluid and frozen in place. Thus, ice sample 22 is securely fastened to frame 24. Frame 24 is placed on support material 32 which is in turn fixed on the surface of the earth. Support material 32 is preferably a packed sand base, saturated with water and frozen to secure support material within pit 30. By fixing ice sample 22 within frame 24 and securing backing plate 28 to support material 32, ice sample 22 approximates a semi infinite mass. The provision of a semi infinite mass is essential for ice impact testing since a large ice mass, such as an iceberg, traveling at the rate of approximately 1 knot and weighing up to one hundred million tons approximates a semi infinite mass. In order to obtain impact data for an ice mass such as an iceberg, the ice sample tested must approximate a semi infinite mass.

In operation, the total weight of impact device 18 and shaft 20 may be any desired weight which can be controlled by the addition or subtraction of weighs 36. Shaft 20 is drawn to a predetermined height depending upon the impact energy desired. The potential energy E of the impact device 18 may be calculated by the formula E is equal to W times H where W is the weight of the impact device and H is the height of the drop. This potential energy is converted into kinetic energy when the impact device is released. The kinetic energy at impact is equal to $\frac{1}{2}$ M V squared where M is the mass of the impact device and V is its velocity at the instant of impact. By equating the potential and kinetic energy, the velocity V at impact equals the square root of 2 g H where g is the gravitational constant. Shaft 20 is drawn up through guide cylinder 16 and is releasably held in place until testing is desired. An impact test is performed by releasing shaft 20 from guide cylinder 16 allowing impact device 18 to drop on ice sample 22. The pressure of the impact may be determined by a pressure gage 38 mounted on the nose of spherical head 34 as illustrated in FIG. 2.

The deceleration of the impact device 18 is measured continuously in time by accelerometer 42. The force F of impact is obtained by multiplying the mass of the impact device 18 by the acceleration. The contact area A is determined from the distance D that the impact device 18 penetrates into the ice sample 22 by the formula $A = D\pi(2R - D)$ where R is the radius of the impact device 18 and $\pi$ is the mathematical constant 3.14---. The penetration distance D can be obtained by integrating the acceleration twice or by a special distance measuring device.

Dividing the force F by the contact area A provides a continuous record in time of the average impact pressure. Comparison of the average impact pressure to the measured impact pressure from gage 38 will indicate how uniform the pressure is over the contact area.

Ring 26 of frame 24 provides a biaxial support for ice sample 22. Ring 26 provides support in the X and Y directions on a three dimensional Cartesian coordinate system. By fixing backing plate 28 to ring 26 a third dimension of support, namely the Z direction, is supplied to provide a triaxial support system for ice impact testing.

The compressional force exerted by impact device 18 affects only outer surface 40 of ice sample 22. As impact device 18 impinges upon outer surface 40 of ice sample 22, crushing of ice sample begins. The crushed ice will be forced out along the surface of spherical head 34. The heat generated by the initial impact will partially melt a portion of ice sample 22. Since ice sample 22 is triaxial confined in the X, Y and negative Z directions, ice sample 22 appears to be a semi infinite mass to impact device 18. As such, ice sample 22 will not fracture or crack in response to the force exerted by impact device 18, but will act similar to the manner in which an iceberg will react to colliding with a structure such as an offshore platform.

Previously, impact testing of an ice mass such as an iceberg was impossible in a laboratory environment where conditions, such as temperature, could be controlled. By providing a frame means which approximates a semi infinite mass, meaningful impact tests can be performed on ice samples taken from icebergs which permit the defining of structural properties of icebergs.

While the present invention has been illustrated by way of preferred embodiment, it is to be understood that this is for illustration purposes only and the present invention should not be limited thereto but only by the scope of the following claims.

APPENDIX A

Consider a ring with internal radius $r_i$ and external radius $r_o$, under internal pressure q and zero external pressure. The radial displacement u at $r_i$ is $$u = \frac{q \, r_i}{r_o^2 - r_i^2} \left[ \left( \frac{1 + v_s}{E_s} \right) r_o^2 + \left( \frac{1 - v_s}{E_s} \right) r_i^2 \right]$$

where $E_s$ is Young's modulus and $v_s$ is Poisson's ratio of the ring. For a concentrated load P on a semi-infinite ice mass, the radial stress $\sigma$ at a radius of $r_i$ on the surface of the ice is $$\sigma = \frac{P}{2\pi} \frac{(1 - 2v_i)}{r_i^2}$$

and the radial displacement v is $$v = -\frac{P}{2\pi} \frac{(1 - 2v_i)}{r_i} \left( \frac{1 + v_i}{E_i} \right)$$

where $E_i$ is Young's modulus and $v_i$ is Poisson's ratio for the ice. Equating the stresses ($\sigma = -q$) and the displacements ($u = v$) at $r_i$, gives the equation to determine $r_o$ as $$\frac{r_o^2}{r_i^2} = \frac{\frac{1 + v_i}{E_i} + \frac{1 - v_s}{E_s}}{\frac{1 + v_i}{E_i} - \frac{1 + v_s}{E_s}}$$

If $E_s$ is much greater than $E_i$, this equation can be approximated by $$r_o - r_i = \frac{r_i}{1 + v_i} \frac{E_i}{E_s}$$

I claim:
1. A device for testing ice samples comprising:
    impact device for imparting a force to the ice sample;
    structure means for releasably holding and generally guiding said impact device;
    frame means positioned within said structure means below said impact device for receiving the ice sample including a ring for providing biaxial support to the ice sample and a backing sheet coupled to said ring to provide a third axial support, and base means for providing support for said backing sheet, said frame means simulating a semi infinite mass.
2. The device for testing ice samples according to claim 1 wherein said base means includes a pit filled with sand saturated with water and frozen.
3. The device for testing ice samples according to claim 1 wherein said base means includes:
    a concrete base secured to the earth's surface.
4. A method for testing ice samples comprising the steps of:
    securing an ice sample within a triaxial support to simulate a semi infinite mass;
    releasably supporting an impact device at a predetermined height above said ice sample; and
    dropping said impact device on said ice sample to impart a impact force on said ice sample.
5. In an ice sample impact testing system, an ice sample holder comprising:
    biaxial means for providing support along two directional axes of the ice sample;
    uniaxial means secured to said biaxial means for providing a third directional axes support for the ice sample; and
    support means for receiving said uniaxial means and securing said uniaxial means to the surface of the earth.

6. The ice sample holder according to claim 5 wherein said support means includes a sand filled pit saturated with water and frozen.

7. The ice sample holder according to claim 5 wherein said support means includes a concrete slab.

8. The ice sample holder according to claim 5 wherein said biaxial means includes an annular shaped ring.

9. The ice sample holder according to claim 5 wherein said uniaxial means includes a backing sheet secured to said biaxial means.

* * * * *